United States Patent
Angelsen et al.

(10) Patent No.: US 7,641,613 B2
(45) Date of Patent: Jan. 5, 2010

(54) ULTRASONIC CONTRAST AGENT DETECTION AND IMAGING BY LOW FREQUENCY MANIPULATION OF HIGH FREQUENCY SCATTERING PROPERTIES

(76) Inventors: Bjørn A. J. Angelsen, Bugges weg 4b, Trondheim (NO) 7051; Rune Hansen, Kaarli, Stadsbygd (NO) 7105

( * ) Notice: Subject to any disclaimer, the term of this patent is extended or adjusted under 35 U.S.C. 154(b) by 1058 days.

(21) Appl. No.: 10/864,992

(22) Filed: Jun. 10, 2004

(65) Prior Publication Data

US 2004/0267130 A1 Dec. 30, 2004

Related U.S. Application Data

(63) Continuation of application No. 10/851,820, filed on May 21, 2004, now abandoned.

(60) Provisional application No. 60/475,222, filed on May 30, 2003.

(51) Int. Cl.
*A16B 8/00* (2006.01)
(52) U.S. Cl. .................................................... 600/458
(58) Field of Classification Search ................ 600/458, 600/437, 448
See application file for complete search history.

(56) References Cited

U.S. PATENT DOCUMENTS

| | | | |
|---|---|---|---|
| 4,483,345 A * | 11/1984 | Miwa ........................... 600/438 |
| 4,610,255 A * | 9/1986 | Shimura et al. ............. 600/443 |
| 4,844,082 A * | 7/1989 | Fukukita et al. ............ 600/442 |
| 5,961,464 A * | 10/1999 | Poland ....................... 600/458 |
| 6,186,951 B1 | 2/2001 | Lizzi et al. |
| 6,238,342 B1 | 5/2001 | Feleppa et al. |
| 6,312,383 B1 * | 11/2001 | Lizzi et al. .................. 600/437 |
| 6,423,007 B2 | 7/2002 | Lizzi et al. |
| 6,488,626 B1 | 12/2002 | Lizzi et al. |
| 6,514,204 B2 | 2/2003 | Alam et al. |
| 6,533,726 B1 | 3/2003 | Lizzi et al. |
| 6,726,627 B1 | 4/2004 | Lizzi et al. |
| 6,846,290 B2 | 1/2005 | Lizzi et al. |
| 7,198,601 B2 * | 4/2007 | Kanda et al. ................. 600/458 |
| 2004/0236222 A1 * | 11/2004 | Mao et al. .................... 600/458 |
| 2006/0058677 A1 * | 3/2006 | Okada et al. ................. 600/459 |

* cited by examiner

*Primary Examiner*—Eric F Winakur
*Assistant Examiner*—Lawrence N Laryea
(74) *Attorney, Agent, or Firm*—Cohen Pontani Lieberman & Pavane LLP

(57) ABSTRACT

A method for improved detection and imaging of ultrasound contrast agents using dual-band transmitted pulses, is described. The method is based on transmitting a pulse consisting of two frequency bands, a low frequency band which purpose is to manipulate the high frequency scattering properties of the contrast agent, and a high frequency band from which the image reconstruction is based. In addition, a general form of pulse subtraction is used to significantly suppress the received tissue signal.

9 Claims, 8 Drawing Sheets

1 a)

1b)

2a)

2 b)

3 a)

3b)

4a)

4b)

5a)

5b)

6a)

6b)

ULTRASONIC CONTRAST AGENT DETECTION AND IMAGING BY LOW FREQUENCY MANIPULATION OF HIGH FREQUENCY SCATTERING PROPERTIES

CROSS REFERENCE TO RELATED APPLICATIONS

This application is a continuation of U.S. patent application Ser. No. 10/851,820 filed May 21, 2004 now abandoned which claims priority from U.S. Provisional Patent Application Ser. No. 60/475,222 filed May 30, 2003.

BACKGROUND OF THE INVENTION

1. Field of the Invention

This invention relates to methods and systems for ultrasonic detection and imaging of contrast agents located in soft tissue or tissue fluids.

2. Description of the Related Art

Ultrasound contrast agents are typically made as solutions of micro gas bubbles or nano lipid particles. The gas bubbles typically show strong and nonlinear scattering of the ultrasound, a phenomenon that is used to differentiate the contrast agent signal from the tissue signal. In the earliest applications (~1985) the increased scattering from the contrast agent within the transmitted frequency band was used to enhance the scattering from blood. Later, second harmonic components in the nonlinearly scattered signal were used to further enhance the contrast agent signal above the tissue signal in methods generally referred to as nonlinear contrast harmonic imaging.

The following two signal power ratios have vital importance for the quality of performance of a contrast imaging system:

CTR—Contrast signal to Tissue signal Ratio. This gives the ratio of the signal power scattered from the contrast agent in a region to the signal power scattered from the tissue in that region. This ratio is often referred to as specificity.

CNR—Contrast signal to Noise Ratio. This gives the ratio of the signal power scattered from the contrast agent in a region to the noise power in that region. This ratio is often referred to as sensitivity.

The CNR determines the maximum depth for imaging the contrast agent while the CTR describes the enhancement of the contrast agent signal above the tissue signal in the image and thus the capability of differentiating contrast signal from tissue signal. High values of both these ratios are therefore necessary for good imaging of the contrast agent.

The nonlinear distortion of the signal scattered from the contrast agent is much stronger than for the tissue signal, a phenomenon that is extensively used to enhance the CTR. In one method, received tissue signal components in the transmitted frequency band (linear components) are reduced by combining the received signal from two transmitted pulses with different amplitudes. In other methods, the second harmonic band of the nonlinearly scattered signal is obtained either by bandpass filtering or by combining the received signals from two or more transmitted pulses with different polarities.

The contrast agent will typically undergo strong nonlinear oscillations with significant amount of energy scattered at higher harmonic components only if driven into oscillations well below its resonance frequency and the harmonic component used for detection and imaging is often obtained in a bandpass filtering process. To obtain distinct scattered harmonic components, the drive pulse typically has to be relatively narrowbanded. The consequence of a relatively narrowbanded and low frequency drive pulse is the low image resolution typically obtained with harmonic imaging.

Also, the received nonlinear harmonic component from the contrast agent typically has low amplitude which reduces the CNR and may require so high transmitted amplitude that the contrast agent bubbles are destroyed. This can cause a problem when the inflow rate of contrast agent to the tissue region is low.

In addition, nonlinear contrast components scattered in the forward propagation direction will add in phase with the transmit field and hence accumulate. In tissue regions beyond a contrast filled area, these nonlinear contrast components may be linearly back-scattered from the tissue and falsely interpreted as contrast agent signal, hence reducing the CTR. Finally, a limitation in all methods based on nonlinear harmonic detection is that nonlinear components in the tissue signal is preserved in the process, also limiting the CTR.

The new method described does not require nonlinear harmonic imaging and is therefore not constricted by the above mentioned limitations encountered in nonlinear contrast harmonic imaging techniques.

SUMMARY OF THE INVENTION

Ultrasound pulses containing both a low frequency band and a high frequency band overlapping in the time domain, are transmitted towards the ultrasound contrast agent embedded in the tissue. The low frequency components are used to manipulate the acoustic scattering properties of the contrast agent for frequency components in the transmitted high frequency band, and the scattered bubble signal from the high frequency transmitted components is used for image reconstruction. The low frequency components in the received signals can for example be removed through bandpass filtering of the signals around the high frequency band.

The tissue signal is suppressed by transmitting at least two such dual-band pulses for each radial image line with different phases and/or amplitudes between the low and high frequency components, and performing a linear combination of the back-scattered signals from the different pulses.

Due to nonlinear tissue elasticity, the transmitted low frequency pulse will slightly influence the wave propagation of the transmitted high frequency pulse resulting in slightly different high frequency sound speeds when altering the phase and/or amplitude of the low and high frequency pulses. The resulting echoes may then have to be digitally interpolated and adjusted relative to each other before combination to adequately suppress the high frequency tissue echoes.

With non-moving, temporary stationary tissue, one can for example transmit two pulses with different phase of the low frequency components and the same phase of the high frequency components, and perform a linear combination of the back-scattered signals from the two pulses. The scattered high frequency components from the contrast bubble will be manipulated differently than from the tissue by the two low frequency pulses of different phases and/or amplitudes, and the bubble signal can be preserved while the tissue signal is heavily suppressed in the combination of the two echoes.

When the tissue is moving, one may have to transmit more than two pulses for each radial image line to adequately suppress the received tissue signal. For example, one can transmit a set of M pulses, all with the same phase of the high frequency components, but with different phases and/or amplitude of the low frequency components for each pulse. The back-scattered signals from these pulses are combined in a pulse to pulse high-pass filter as is commonly done in ultrasound imaging of blood velocities to suppress the tissue signal.

With electronic steering of the beam direction one would use the same beam direction and focus for all the pulses that are combined to suppress the tissue signal for each radial image line. Typical filtering schemes that are used are FIR-type filters or orthogonal decomposition using for example Legendre polynomials, with filtering along the pulse number coordinate for each depth.

With mechanical scanning of the beam direction, as with annular arrays, one would typically transmit pulses with variations in the phase and/or amplitude of the low frequency components as the beam direction is swept continuously, feeding the signal for each depth to a high pass filter along the pulse number coordinate. The outputs of the high pass filters are then sampled for each depth and radial image line to give the contrast agent signal, with suppression of the tissue signal, to be used for image reconstruction.

The present invention significantly increases the CNR relative to existing methods by using the total scattered high frequency signal, and in particular the strong linear components, from the contrast agent and not only nonlinear components of it.

Relative to nonlinear harmonic imaging methods, the present invention can use a more broadbanded transmit pulse and will hence achieve a higher range image resolution.

In addition, a higher transmit frequency can be used resulting in a significant increase in both lateral and range resolution relative to nonlinear imaging methods.

The performance of the present invention will not be sensitive to the amplitude of the imaging pulses compared to nonlinear imaging methods. Together with the indicated suppression of received tissue signal with resulting increase in CNR, this facilitates nondestructive detection and imaging of single contrast agent bubbles.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

DETAILED DESCRIPTION OF THE PRESENTLY PREFERRED EMBODIMENTS

The invention will now be described in more detail with reference to the figures.

For small amplitude radius excursions, the mathematical equations governing contrast bubble oscillation can be linearized and we obtain the following transfer function from incident pressure on the bubble surface to radial bubble displacement $$H_1(\Omega) = \frac{1}{\Omega^2 - 1 - i\Omega d}$$

where $$d = \frac{b}{\omega_0 m}, \quad \omega_0^2 = \frac{s}{m}, \quad \Omega = \frac{\omega}{\omega_0}$$

Here, $\omega$ is the angular frequency and $\omega_0$ is the resonance frequency of the bubble while s is the stiffness of the gas and shell, m is the inertia of the surrounding liquid, and d is a damping factor of the resonant system.

Figure 1:
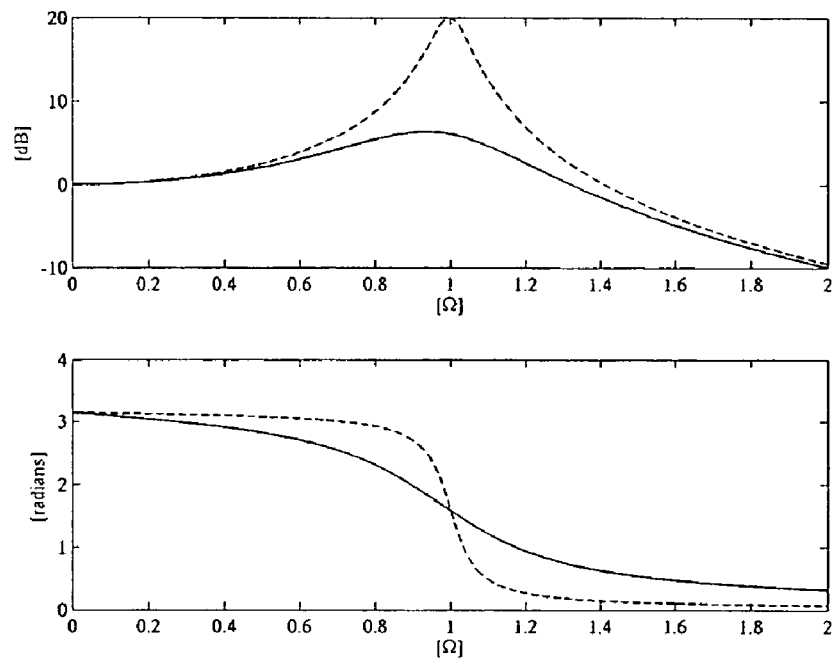
FIG. 1 displays the transfer functions from drive pressure to radial oscillation and to scattered pressure of a contrast bubble undergoing small amplitude oscillations.
Figure 1:
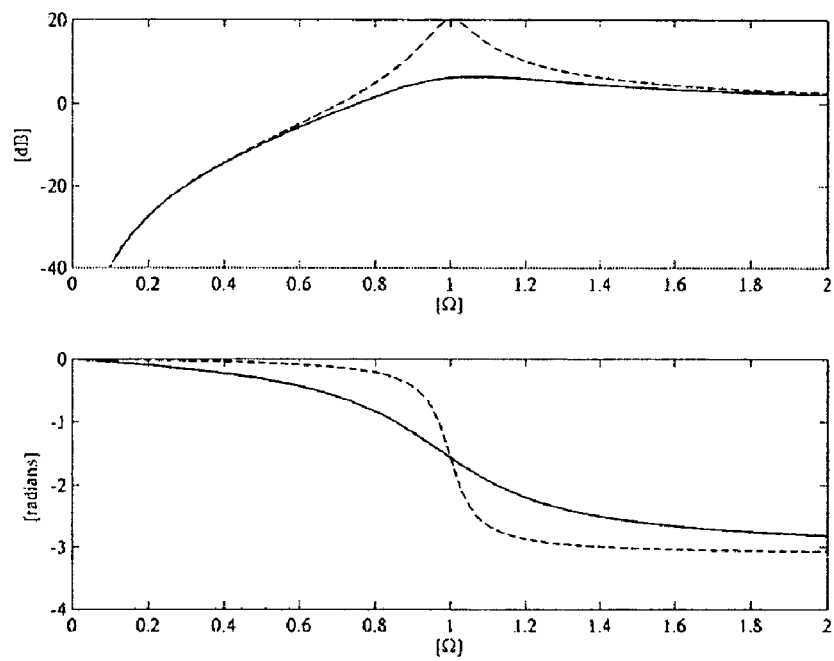

The absolute value and phase angle of $H_1(\Omega)$ is shown in the upper and lower panel in FIG. 1a, respectively. In the lower panel, we see that for drive frequencies well below resonance the displacement is $\pi$ out of phase with the driving pressure. For frequencies well above resonance the bubble responds differently and the displacement and drive pressure are now in phase so that the bubble is increased in size when the drive pressure is positive and vice versa. Around resonance the displacement is approximately $\pi/2$ out of phase with the drive pressure. The absolute value of the amplitude of the transfer function is seen in the upper panel of FIG. 1a. Going from frequencies below resonance towards resonance the amplitude increases gradually culminating with a prominent peak around resonance for the situation with low damping (dashed line, d=0.1) and a considerable smaller peak for the situation with higher damping (solid line, d=0.5). In both cases, the amplitude decreases rapidly above resonance.

The transfer function from incident pressure on the bubble surface to scattered far-field pressure for this small amplitude linearized situation is $$H_2(\Omega) = \frac{\Omega^2}{1 - \Omega^2 + i\Omega d}$$

FIG. 1b displays the absolute value and phase angle of $H_2(\Omega)$ in the upper panel, while the phase angle of $H_2(\Omega)$ is shown in the lower panel. As previously, the dashed lines are results obtained setting the parameter d equal to 0.1 while the solid lines are obtained for d equal to 0.5. The amplitude of the scattered pressure, as seen from the upper panel in FIG. 1b, significantly increases when going from drive frequencies below resonance towards resonance. For drive frequencies above resonance, the scattered amplitude approaches a constant level. In the lower panel of the figure, we see that the phase for drive frequencies well below resonance, the scattered pressure is in phase with the driving pressure. This means that the bubble oscillation is dominated by s, the stiffness of the gas and shell. For frequencies well above resonance, the bubble responds differently and the oscillation is now dominated by m, the inertia of the co-oscillating fluid mass. The scattered pressure and drive pressure are now $\pi$ out of phase as seen in the lower panel of FIG. 1b. Around resonance the scattered pressure is approximately $\pi/2$ out of phase with the drive pressure.

The purpose of the present invention is to heavily suppress the high frequency tissue echoes in the image while maintaining the total high frequency contrast agent echoes, and the essence of the invention is now described, by way of example, through applying a simple two-pulse transmit scheme for each radial image line.

Figure 2:
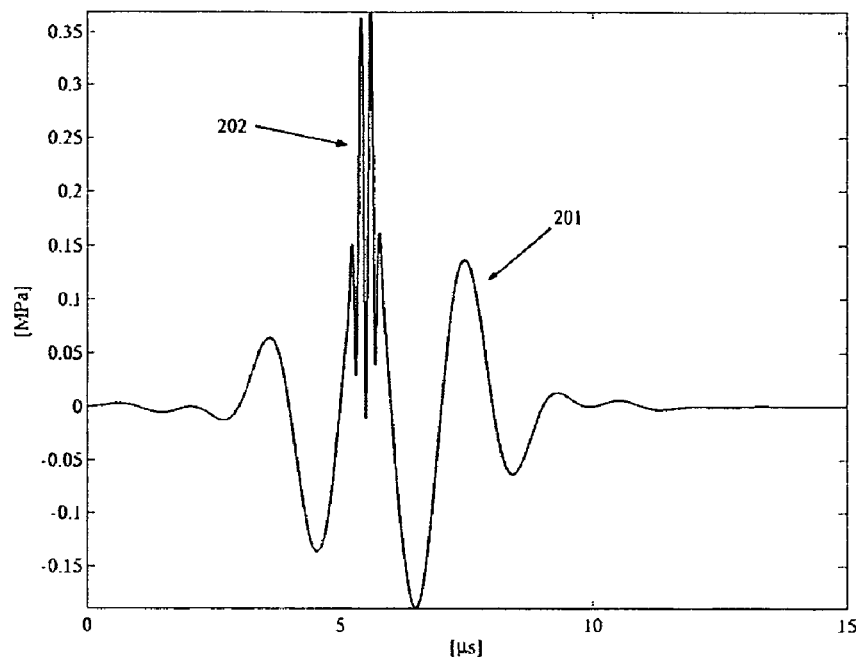
FIG. 2 illustrates transmit pulses containing both a low frequency pulse and a high frequency pulse where the high frequency pulse is placed in the peak positive or peak negative period of the low frequency pulse.
Figure 2:
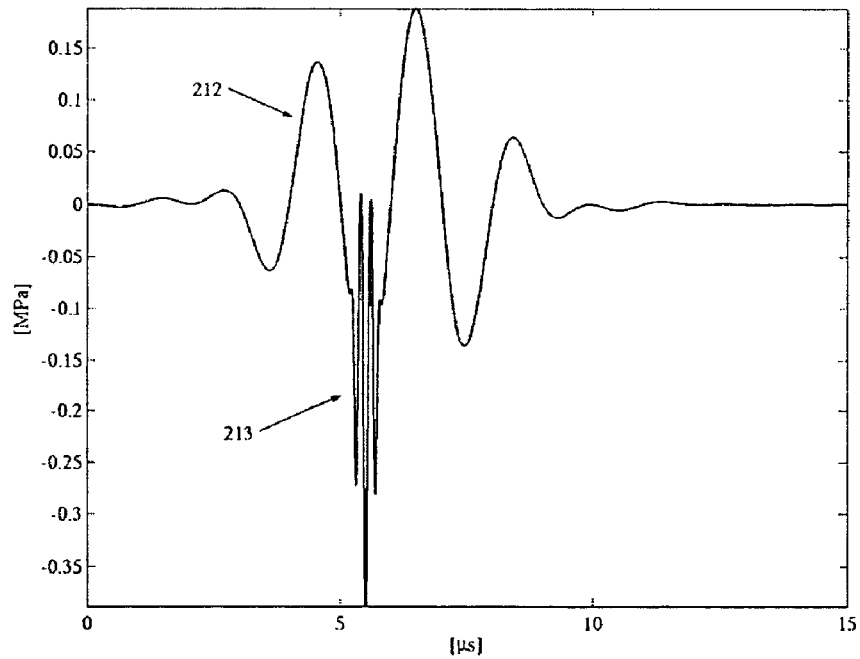

In the first transmitted dual-band pulse, the high frequency component 202 is placed in the positive peak of the low frequency component 201 as shown in FIG. 2a, whereas in the second transmitted pulse, the high frequency component 213 is placed in the negative peak of the low frequency component 212 as shown in FIG. 2b. The difference between FIG. 2a and FIG. 2b is that the polarity of the transmitted low frequency components are inverted with respect to each other. In other example embodiments according to the invention, the phases between two low frequency pulses may vary with a different value ($\neq \pi$), with possible variation in the amplitude of the low frequency pulses between the two low frequency pulses, even without variation of the phase.

Figure 3:
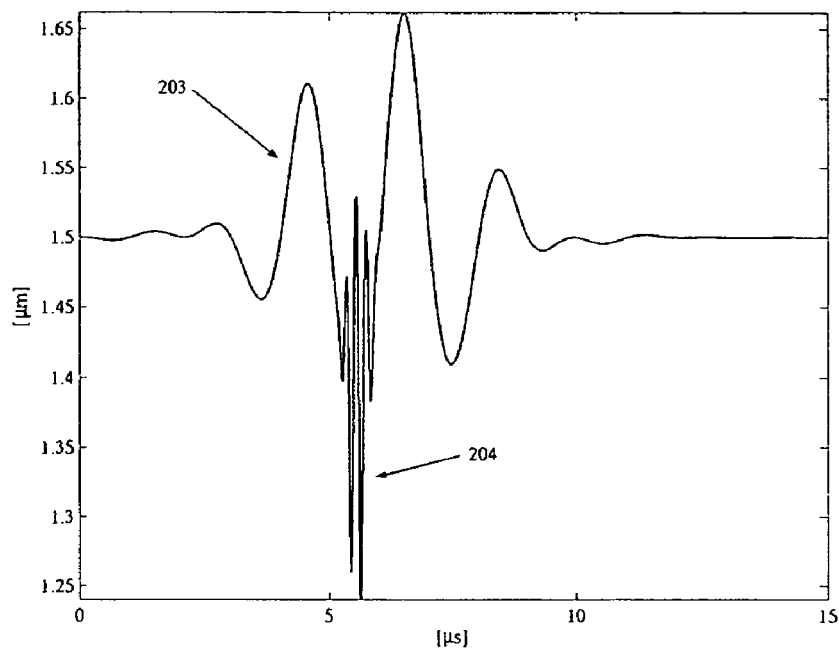
FIG. 3 shows the radius responses from a bubble with resonance frequency around 4 MHz when driven by the pressure pulses in FIG. 2.
Figure 3:
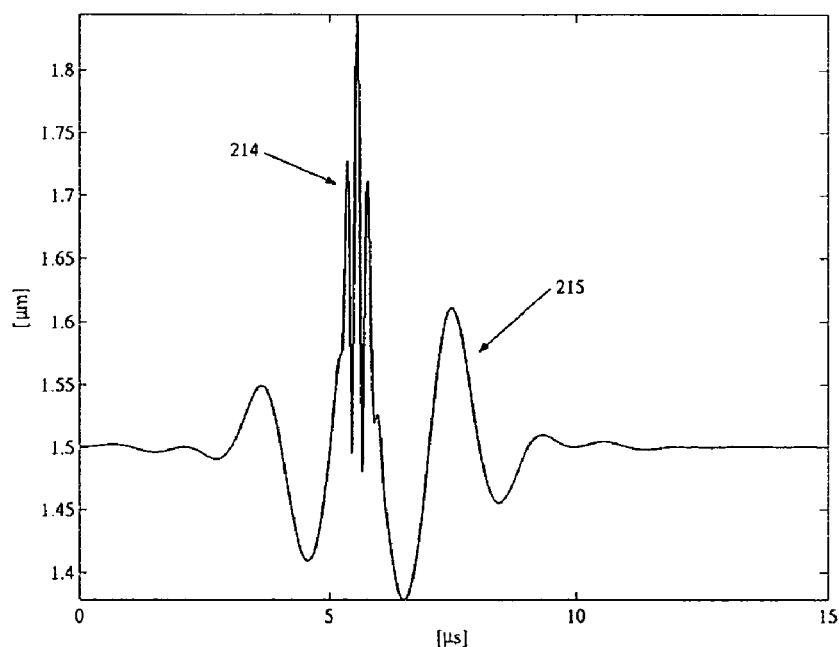

FIG. 3a shows the radius response from a contrast bubble with resonance frequency around 4 MHz when driven by the pulse in FIG. 2a while the radius response from the same bubble when driven by the pulse in FIG. 2b is seen in FIG. 3b. The high frequency components (202 and 213) in the transmitted pulses are here around 5 MHz and hence chosen to be in the same area as the equilibrium resonance frequency of the contrast bubble. This is, however, done only for purpose of illustration and not a limitation in the present invention. From the bubble radius oscillations, it is seen that the high frequency component in the first transmitted pulse occurs when the bubble is compressed (204) by the low frequency pulse, whereas the high frequency component in the second transmitted pulse occurs when the bubble is expanded (214) by the low frequency pulse. When compressed, the bubble will increase its resonance frequency, while when expanded, it will reduce its resonance frequency.

From FIG. 1a we see that both the amplitude and phase angle of the radius oscillation will change for a given drive frequency when changing the resonance frequency of the bubble.

Figure 4:
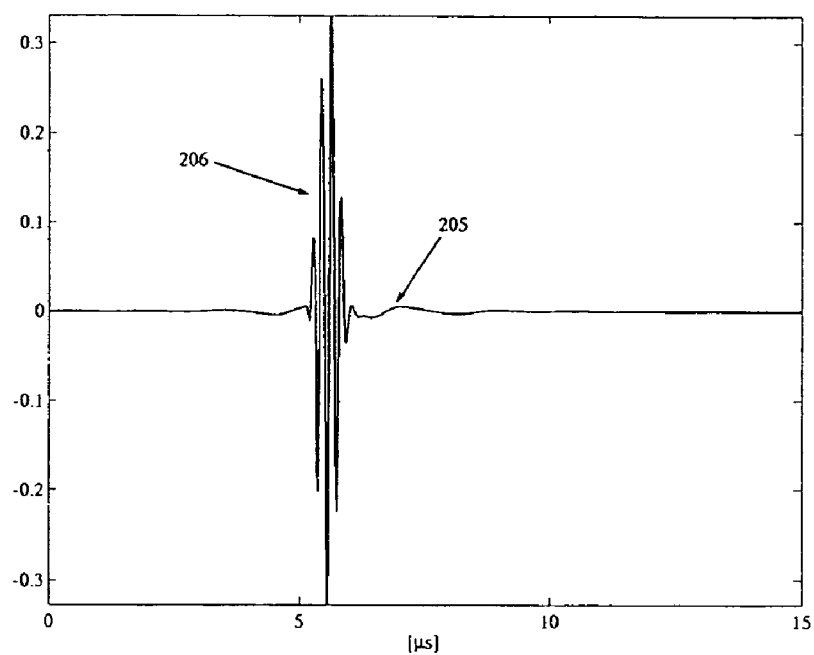
FIG. 4 shows the far-field scattered pressure pulses from a bubble with resonance frequency around 4 MHz when driven by the pressure pulses in FIG. 2.
Figure 4:
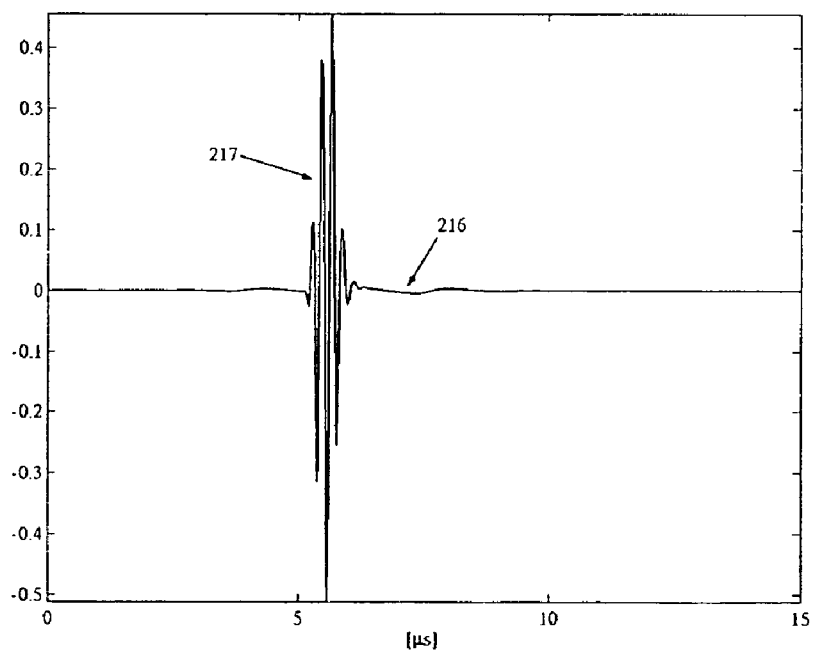
Figure 5:
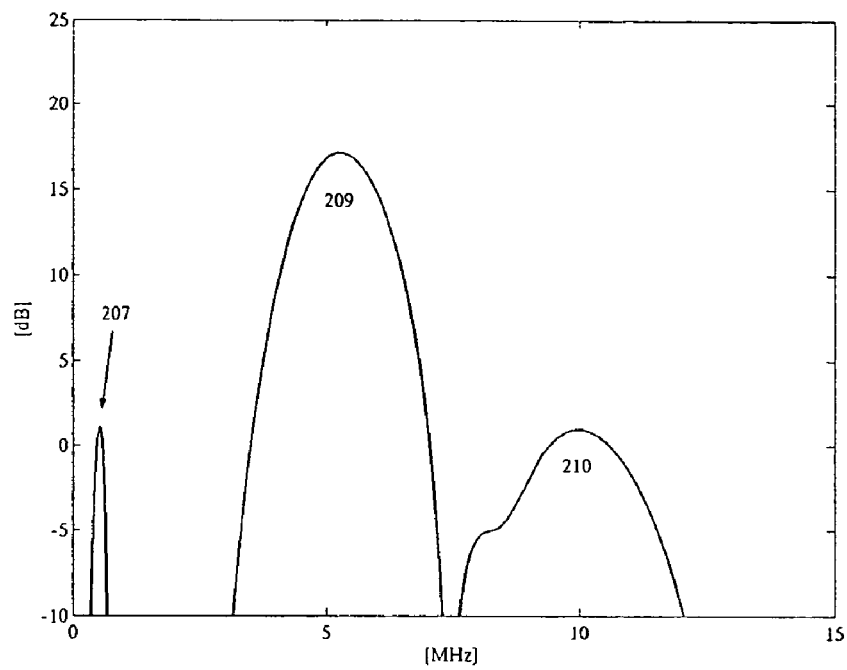
FIG. 5 depicts the absolute value of the Fourier Transform of the pressure pulses in FIG. 4.
Figure 5:
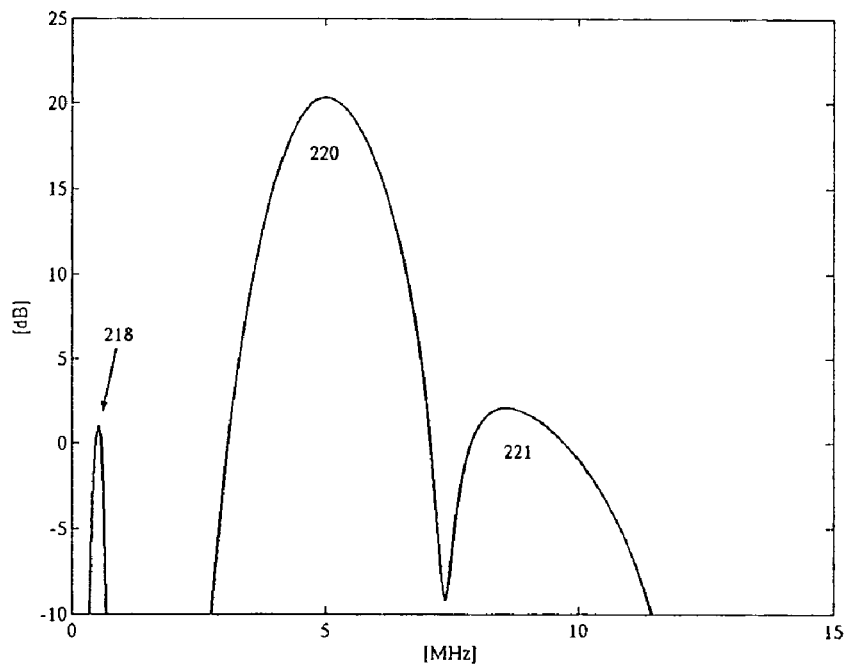

The resulting far-field scattered pressure from the contrast bubble when driven by the incident pressure pulse in FIG. 2a is depicted in time domain in FIG. 4a and in frequency domain in FIG. 5a, while the scattered pressure obtained when driven by the incident pulse in FIG. 2b is depicted in time domain in FIG. 4b and in frequency domain in FIG. 5b. The scattered high frequency fundamental component (209) in FIG. 5a is somewhat weaker than the scattered high frequency fundamental component (220) in FIG. 5b. Nonlinear scattered high frequency components (210 and 221) are also somewhat different. Scattered low frequency components (207 and 218) have low amplitude and are not meant to be used for image reconstruction. The purpose of the low frequency components is only to manipulate the scattering properties of the contrast agent, i.e. to make the bubble oscillate with such a low frequency that high frequency components can be used to interrogate it while manipulated by the low frequency pulses.

From FIG. 1b we notice that both the amplitude and phase angle of the scattered pressure will vary for a given drive frequency when varying the resonance frequency as done when manipulating the bubble by the low frequency pulses.

Figure 6:
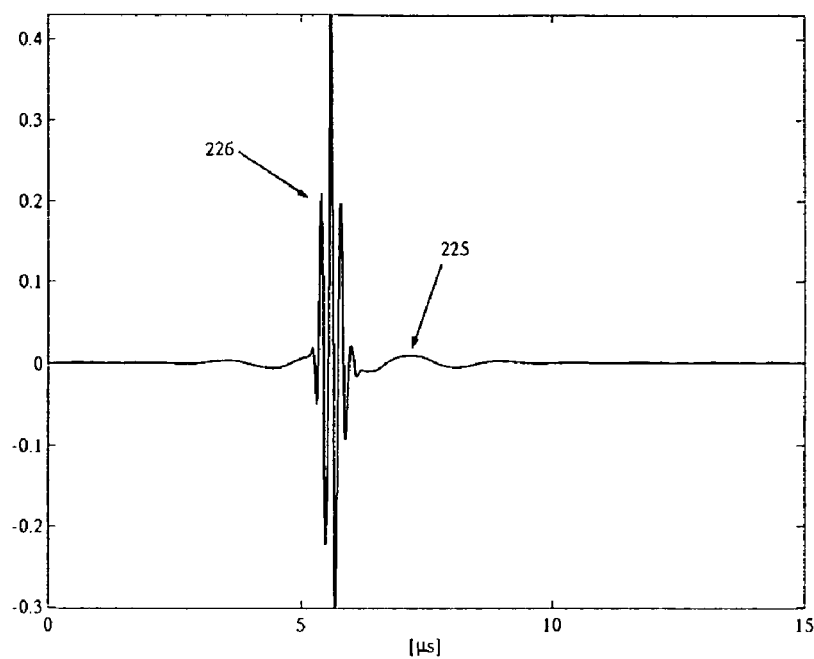
FIG. 6 displays the result obtained by subtracting the two scattered contrast pulses in FIG. 4 so that the high frequency tissue components can be suppressed.
Figure 6:
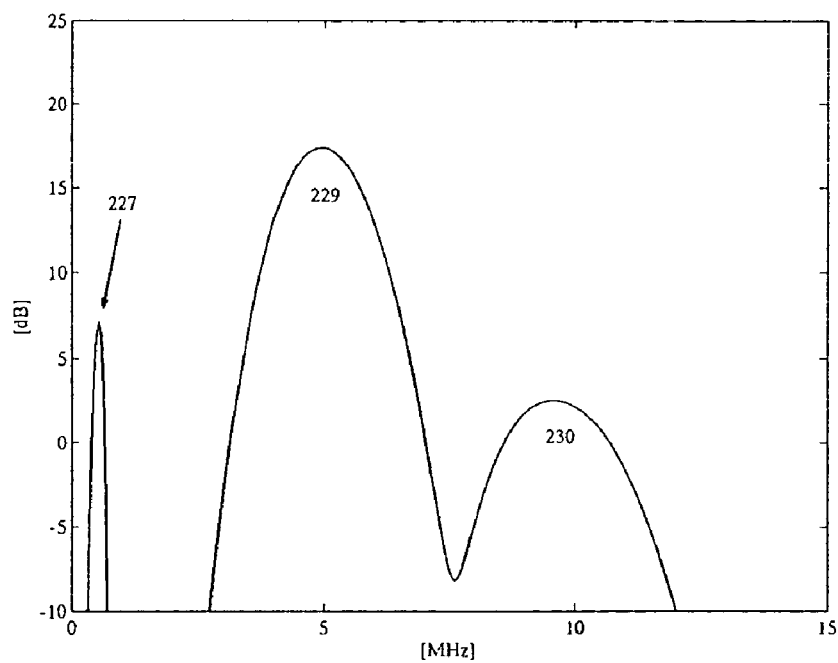

To suppress the tissue signal the two scattered pressure pulses in FIG. 4 are then subtracted and the result is depicted in time domain in FIG. 6a. In FIG. 6b, we see the spectrum of the resulting pulse. We notice that even if the two high frequency drive pulses in FIG. 2 occur at the exact same relative time from the pulse start, due to the manipulation by the low frequency pulses, the scattered high frequency energy from the bubble is not canceled or significantly reduced in the subtraction process of the two bubble echoes. We may thus utilize the total scattered high frequency energy from the bubble for image reconstruction and not only a nonlinear component of it as done in all non-destructive nonlinear contrast agent detection techniques.

It is also possible to use two transmit pulses where one of the transmit pulses only contains the high frequency imaging pulse whereas the other transmit pulse contains both the manipulating low frequency pulse and the high frequency imaging pulse overlapping in the time domain. This would then be a version of amplitude modulation for the low frequency transmit pulse, as described above. Other variations of the phase and/or the amplitude between the two low frequency pulses are also possible. Due to the large separation in frequency of the low and high frequency pulses, one might use separate transducer elements to transmit the two pulse components. If the low and high frequency transducer elements have different spatial positions, the phase between the high and low frequency pulses can vary with depth. The current method of enhancing the contrast agent signal while suppressing the tissue signal, will however work in such a situation also as the main essence is that the high frequency scattering properties of the bubbles are manipulated between transmitted pulses by the low frequency pulses, with limited change of the signal scattered from the tissue.

When the tissue is moving, it may be advantageously to transmit more than two pulses for each radial image line to adequately suppress the received high frequency tissue signal. For example, one can transmit a set of M pulses, all with the same phase and amplitude of the high frequency components, but with different phases and/or amplitudes of the low frequency components for each pulse. The back-scattered signals from these pulses are combined in a pulse to pulse high-pass filter as is commonly done in ultrasound imaging of blood velocities to suppress the tissue signal.

With electronic steering of the beam direction one would use the same beam direction and focus for all the pulses that are combined to suppress the tissue signal for each radial image line of the contrast agent image. Typical filtering schemes that are used are FIR-type filters or orthogonal decomposition using for example Legendre polynomials, with filtering along the pulse number coordinate for each depth.

With mechanical scanning of the beam direction, as with annular arrays, one would typically transmit pulses with variations in the phase and/or amplitude of the low frequency components as the beam direction is swept continuously, using the signal for each depth as inputs to high pass filters along the pulse number coordinate, as is commonly done in Doppler blood velocity imaging. The outputs of the high pass filters are then sampled for each depth and radial image line to give the contrast agent signal, with suppression of the tissue signal, to be used for image reconstruction of the contrast agent image.

Acoustic wave propagation is in the linear regime governed by the linear wave equation where the speed of sound is defined as $$c_0 = \frac{1}{\sqrt{\rho\kappa}}$$

where $\rho$ is the density and $\kappa$ is the compressibility of the propagation medium. Due to nonlinear tissue elasticity we get, based on a plane wave approximation, a nonlinear propagation velocity that depends on the wave pressure as $$c = c_0\sqrt{1+2\beta\kappa p - 2\beta^2(\kappa p)^2} \approx c_0(1+\beta\kappa p)$$

where $\beta$ is a nonlinearity parameter accounting for nonlinear intermolecular forces in the propagation medium and p is the acoustic pressure. The last approximation is valid for the case when $\kappa p \ll 1$. In medical ultrasound imaging, $\kappa p$ typically lies in the range from $2 \cdot 10^{-3}$ to $2 \cdot 10^{-5}$ whereas $\beta$ is around 5.

Ultrasound wave propagation in tissue is hence a weak nonlinear process for intensities commonly applied in medical imaging. Due to the nonlinear tissue elasticity, the high frequency components of the two dual-band pulses displayed in FIG. 2 can have slightly different propagation velocities. The high frequency component (202) in FIG. 2a, occurring during the positive pressure swing of the low frequency component, will travel with a slightly higher sound speed than the high frequency component (213) in FIG. 2b, occurring during the negative pressure swing of the low frequency component. Using Eq. 12 with $c_0$ equal to 1500 m/s, we get a typical sound speed of 1500.5 m/s for the transmitted high frequency component in FIG. 2a and 1499.5 m/s for the high frequency component in FIG. 2b.

The consequence of this difference in sound speed is that the two resulting high frequency echoes obtained from the indicated transmit pulses may have to be slightly time-shifted relative to each other before combined to adequately suppress the tissue echoes. These time-shifts are typically smaller than the sampling interval of the signal which requires interpolation for adequately accurate signal values.

Figure 7:
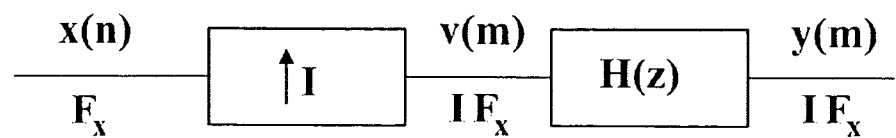
FIG. 7 illustrates the method of digital sampling rate increase (interpolation)

FIG. 7 displays schematically an interpolation method of sampling rate increase by a factor of I. The interpolation is here done by first introducing I-1 zeros between each sample in the original sequence x(n) with a sampling rate of $F_x$ to obtain the desired sampling rate $IF_x$.

Mathematically, the resulting sequence can be described as $$v(m) = \sum_{m=-\infty}^{\infty} x(m/I)$$

for m=0,±I,±2I, . . . and v(m)=0 otherwise

The sequence v(m) is then passed through a lowpass filter h(m) to obtain the desired output y(m) and this lowpass filter is typically implemented as a linear phase FIR-type filter where the z-transform of the filter is defined as $$H(z) = \sum_{k=0}^{M-1} h(k)z^{-k}$$

for a filter of length M.

Figure 8:
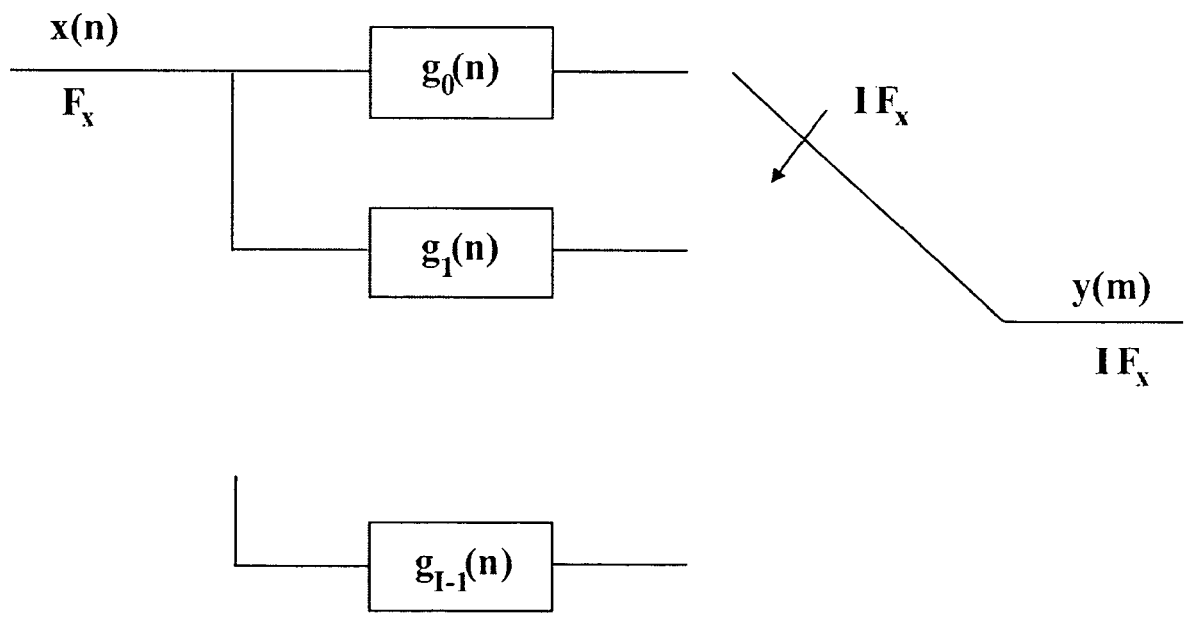
FIG. 8 shows a realization of the interpolation process by the use of polyphase filters.

The direct-form realization of the interpolation algorithm is computationally not very efficient due to all the zeros in the sequence v(m). To increase the efficiency, the filter h(m) can be divided into a set of smaller filters of length K=M/I, where M is selected to be a multiple of I. This set of smaller filters are usually called polyphase filters and have unit sample responses $g_k(m)=h(k+mI)$ for $k=0,1,\ldots,I-1$ and $m=0,1,\ldots,K-1$ Thus, the polyphase filters perform the computations at the original low sampling rate $F_x$ and the rate conversion results from the fact that I output samples are generated, one from each of the filters, for each input sample. Interpolation by use of polyphase filters are shown schematically in FIG. 8. Here, the polyphase filters are arranged as a parallel realization and the output of each filter is selected by a commutator rotating in the counterclockwise direction. The decomposition of h(m) into the set of I subfilters with impulse responses $g_k(m)$ results in filtering of the input samples x(n) by a periodically time-varying linear filter g(m,k).

Figure 9:
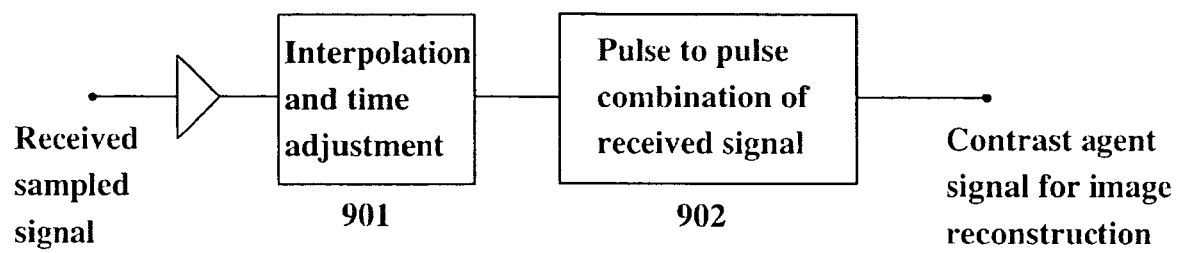
FIG. 9 shows schematically the adjustment and combination of received echoes done in order to suppress the high frequency tissue components.

FIG. 9 shows schematically the adjustment and combination process done to suppress the received high frequency tissue signal components. The received echoes are first temporally interpolated and given a variable time adjustment (901) before the pulse to pulse combination (902) to heavily suppress the high frequency tissue components.

One should note that the time delay effect of this variation in propagation velocity of the high frequency pulse is an integrating effect along the beam depth. With spatial offset between the transducer elements for the low and high frequency pulses, the phase between the high and low frequency pulses may even vary in sign along the beam depth for the same transmit pulse, as described above. In this case, the induced variation of the high frequency pulse propagation velocity by the low frequency pulse has less total effect on the delay of the high frequency pulses between different transmissions, compared to when the phase between the high and low frequency components stays fairly constant along the beam.

The separated contrast agent image is typically shown as an overlay with different color or pattern of the standard tissue image as obtained with only one of the transmit pulses for each radial image line.

A weak tissue background in the ultrasound image can be obtained by using inaccurate or no time adjustments of the high frequency pulses with different phases of the low frequency pulses. Some of the tissue signal power can thus be brought to partly pass through the high pass filter for tissue signal cancellation.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

We claim:

1. A method for detection and imaging of ultrasound contrast agent in a region of soft tissue, comprising:
    transmitting at least two ultrasound pulse complexes toward said region, each of said at least two ultrasound pulse complexes includes a low frequency (LF) pulse and a high frequency (HF) pulse with the same or overlapping beam directions and that overlap in time at least for part of an image depth, wherein at least one of a frequency, an amplitude and a phase of said LF pulse relative to said HF pulse varies for each transmitted pulse complex;
    receiving scattered signals from the HF pulse component of each of the at least two ultrasound pulse complexes, the scattered signals being scattered by the ultrasound contrast agent in the region of the soft tissue; and
    time delay adjusting and combining the received scattered signals from at least two of said HF pulse components to provide image signals that essentially contain components scattered from contrast agent micro bubbles with strong suppression of signal components scattered from tissue.

2. A method according to claim 1, wherein a magnitude of a time delay in said step of time delay adjusting is for several depths calculated using a pressure dependent variation of propagation velocity given by the formula $$c(p_{LF}) = c_0(1 + \beta_n \kappa p_{LF})$$

for wave propagation velocity and its dependence of the LF pulse pressure $p_{LF}$ at the location of the HF pulse as a function of depth with selected material parameters $\beta_n \kappa c_0$ and an estimate of the LF pulse pressure at the location of the HF pulse at several depths.

3. A method according to claim 2, where said time delay is at various depths first calculated according to the given formula and further manually adjusted for improved suppression of the tissue signal.

4. A method according to claim 1, wherein a time delay in said step of time delay adjusting is manually adjusted at different depths for suppression of the tissue signal.

5. A method according to claim 1, wherein time delay adjustments in said step of time delay adjusting include interpolation of the signals before combination to produce image signals from said contrast agent.

6. A method according to claim 1, further comprising the step of separately adjusting in said transmitted pulses the amplitude of said transmitted high frequency pulses.

7. A method according to claim 1, further comprising manipulating acoustic scattering properties of said contrast agent using the low frequency components of said at least two ultrasound pulse complexes.

8. A method according to claim 1, further comprising the step of showing a resulting contrast agent image as an overlay on a resulting tissue image with a different intensity, color, or pattern.

9. A method according to claim 8, wherein time delay adjustments in said step of time delay adjusting are implemented so that a part of the received high frequency tissue signal remains after the combination and is shown as a weak tissue image overlayed by the contrast agent image.

* * * * *